US005487874A

United States Patent [19]
Gibboney, Jr.

[11] Patent Number: 5,487,874
[45] Date of Patent: Jan. 30, 1996

[54] AIR INTAKE SYSTEM FOR AN INTERNAL COMBUSTION ENGINE

[75] Inventor: James W. Gibboney, Jr., Conyers, Ga.

[73] Assignee: Scientific Products Corporation, Conyers, Ga.

[21] Appl. No.: 221,103

[22] Filed: Mar. 30, 1994

Related U.S. Application Data

[63] Continuation-in-part of Ser. No. 889,167, May 27, 1992, Pat. No. 5,300,266.

[51] Int. Cl.$^6$ .............................. F02B 75/10; B01J 19/08
[52] U.S. Cl. .............. 422/186.03; 422/186; 422/186.04; 422/186.07; 422/186.13; 422/186.18; 422/186.22; 422/186.26; 422/906; 422/907; 204/156; 204/164; 123/539; 123/536; 123/434; 123/216
[58] Field of Search .............................. 422/186, 186.03, 422/186.04, 186.07, 186.13, 186.18, 186.22, 186.26, 906, 907; 204/156, 164; 123/539, 536, 434, 216

[56] References Cited

U.S. PATENT DOCUMENTS

| | | | |
|---|---|---|---|
| 1,257,053 | 2/1918 | Warman | 204/32 |
| 1,725,661 | 8/1929 | McPartland | 204/32 |
| 1,959,738 | 5/1934 | Nyun | 204/32 |
| 3,005,762 | 10/1961 | Fenn | 422/186 |
| 3,059,910 | 10/1962 | Moriya | 261/72 |
| 3,090,745 | 5/1963 | Berghaus | 422/186 |
| 3,157,172 | 11/1964 | Mittelstaedt | 123/119 |
| 3,332,870 | 7/1967 | Orbach et al. | 422/186 |
| 3,842,286 | 10/1974 | Imris | 250/535 |
| 4,048,668 | 9/1977 | Von Bargen et al. | 361/235 |
| 4,062,748 | 12/1977 | Imris | 204/176 |
| 4,069,665 | 1/1978 | Bolasny | 60/275 |
| 4,138,980 | 2/1979 | Ward | 123/119 E |
| 4,195,606 | 4/1980 | Wallis, Jr. et al. | 123/119 E |
| 4,220,545 | 9/1980 | Franzan et al. | 250/530 |
| 4,221,972 | 9/1980 | Oppel et al. | 250/531 |
| 4,308,844 | 1/1982 | Persinger | 123/539 |
| 4,309,199 | 1/1982 | Suzuki | 55/127 |
| 4,417,966 | 11/1983 | Krauss et al. | 204/176 |
| 4,434,771 | 3/1984 | Slomnicki | 123/539 |
| 4,519,357 | 5/1985 | McAllister | 123/539 |
| 4,818,355 | 4/1989 | Kanter et al. | 204/170 |
| 4,929,319 | 5/1990 | Dinter et al. | 204/164 |
| 5,000,152 | 3/1991 | McCauley | 123/536 |
| 5,002,738 | 3/1991 | Pin et al. | 422/186.13 |
| 5,010,869 | 4/1991 | Lee | 123/539 |
| 5,061,462 | 10/1991 | Suzuki | 422/186.04 |
| 5,098,671 | 3/1992 | Shiota | 422/186.07 |
| 5,111,797 | 5/1992 | Shikanai | 123/539 |
| 5,329,910 | 7/1994 | Tanaka | 123/536 |

*Primary Examiner*—Donald P. Walsh
*Assistant Examiner*—Daniel Jenkins
*Attorney, Agent, or Firm*—Michael A. Mann

[57] ABSTRACT

An apparatus for supplying combustion gas to an internal combustion engine. The apparatus generates negatively-charged molecules of the formula $[MO_x]^-$, where M is a positive ion, O is oxygen and x is a number at least equal to 3, and means for mixing the molecules with combustion gas and fuel supplied to the engine. Molecules $[MO_x]^-$ are produced in an ion generator that comprises a specially shaped anode and cathode spaced apart from each other in a non-conducting housing. When a substantially constant voltage is applied across the anode and cathode, a plasma forms between and around them that in turn forms a magnetic field around the plasma and the anode. Diatomic oxygen molecules enter the housing and are polarized by the magnetic field and the resulting oxygen ions accelerated toward the plasma. The plasma excites and confines the oxygen ions long enough for them to strike the materials forming the cathode and anode, releasing positive ions of the cathode and anode materials which bind together and form charged molecules $[MO_x]^-$. Upon exiting the ion generator, the charged molecules are mixed with air or other combustion gas supplied to the engine. The charged molecules produce a denser, oxygen-enriched air charge, resulting in longer and hotter burns, creating more torque and horsepower for the same percentage of throttle.

20 Claims, 3 Drawing Sheets

AIR INTAKE SYSTEM FOR AN INTERNAL COMBUSTION ENGINE

This application is a continuation-in-part of application Ser. No. 07/889,167, filed May 27, 1992, now U.S. Pat. No. 5,300,266.

BACKGROUND OF THE INVENTION

1. Field of the Invention

The present invention relates to an apparatus for adding negatively charged molecules to the air intake system of an internal combustion engine, said molecules having the formula $[MO_x]^-$, where M is a positive ion, O is oxygen, and $x \geq 3$. In particular, the present invention relates to increasing the forward velocity and density of the air charge supplied to the cylinder by use of these molecules, thereby increasing the cylinder pressure, which in turn increases the engine torque and power output.

2. Discussion of Background

Almost all motor vehicles are powered by gasoline-burning internal combustion engines. This is a matter of concern due to two factors: first, the environmental effects of carbon monoxide, nitrogen oxides and other combustion products that are released to the atmosphere during operation of an internal combustion engine; and second, known reserves of petroleum are limited and prices are subject to fluctuation due to world market conditions. These factors have stimulated efforts to conserve gasoline, develop alterative fuel sources and design more efficient engines.

The efficiency of an internal combustion engine is limited by the following two factors: first, incoming air loses (1) velocity and (2) electrons as it strikes the moving vehicle itself, high pressure air cells and vortices formed around the radiator, fan blades and air filter intake ducts, and the continuously restrictive and disturbed air passages to the target cylinder. The loss of velocity of the air stream of the moving vehicle means less air will be rammed into the cylinder, thereby limiting the burn of the fuel/air mixture, which limits the cylinder pressure, which in turn limits the amount of torque and horsepower produced by the engine. The loss of electrons increases the ambient positive:negative ion ratio. Typically, the ratio of positive to negative ions in air at sea level is between approximately 5:4 and 8:4. Since ions with the same charge tend to repel one another, increasing the positive:negative ion ratio decreases the density of the air. If the density of the air is reduced, less oxygen is carried into the cylinder. This limits the burn of the fuel/air mixture, which in turn limits the cylinder pressure and thus the amount of torque and horsepower produced by the engine.

Automobiles run better after a thunderstorm. This phenomenon is primarily caused by the natural conditions that exist after an electrical storm, namely, the presence of ozone and an increase in the relative amount of negative ions in the air. These conditions increase the efficiency of the internal combustion process by correcting conditions in the engine that decrease efficiency: first, an air charge that has more negative ions is denser than an air charge with a higher positive:negative ion ratio. (The term "air charge" refers to the quantity of air supplied to the cylinder during a single cycle.) Second, an air charge that is rich in negative ions generates a greater forward velocity because the negative ions are attracted to the positive ionic charge that exists in a cylinder after the previous burn, thus increasing the amount of air that enters the cylinder, the burn time and temperature. Third, ozone ($O_3$) contains more oxygen than diatomic oxygen ($O_2$). The combination of a denser air charge and more oxygen, coupled with increased burn time and temperature, increases the cylinder pressure, which increases the engine torque and horsepower output. By increasing the engine's ability to do work, less fuel is used to perform the same work as an engine in a normal situation.

These conditions last for only a short period of time because the concentration of ozone following a thunderstorm is very small (about 1 part per billion (ppb)), and the relative imbalance of negative ions quickly reverts back to the usual 5:4–8:4 positive:negative ion ratio at the earth's surface. For a short time after a thunderstorm, however, engines run more efficiently and use less gasoline.

A number of ozone generators exist, most of them operating on alternating current. There are two known that use direct current, that is, a current that does not change polarity, namely, those described in U.S. Pat. No. 4,417,966 issued to Krauss. et al. and in U.S. Pat. No. 4,048,668 issued to Von Bargen, et al., but these both use a time-varying current level. The former patent describes a device with a current chopped at a frequency of about 350 Hz; the latter describes a pulsed current having a frequency of ten to sixteen kHz. Many presently-available ozone generators operate at elevated pressure or require cooling mechanisms to dissipate the quantities of heat produced in the generation of ozone, therefore, these types of generators are not suitable for use in the operating environment of an internal combustion engine.

There is a need for an air intake system for an internal combustion engine that operates safely and effectively on direct current, and that supplies a controlled, predictable amount of oxygenated, negative ions to the air charge.

SUMMARY OF THE INVENTION

According to its major aspects and broadly stated, the present application is an apparatus for supplying a combustion gas, such as air, to an internal combustion engine. The apparatus includes an ion generator that produces negatively-charged molecules of the formula $[MO_x]^-$, where M is a positive ion, O is oxygen and x is a number at least equal to 3, and means for mixing the molecules with combustion gas and fuel supplied to the engine. Upon exiting the ion generator, the charged molecules are mixed with combustion gas supplied to the engine. The molecules produce a denser, oxygen-enriched air charge, resulting in longer and hotter burns, creating more torque and horsepower for the same amount of fuel.

The ion generator is an important feature of the present invention. The ion generator includes a specially shaped anode and cathode spaced apart from each other in a non-conducting housing. When a substantially constant voltage is applied across the anode and cathode, a plasma forms between and around them that in turn forms a magnetic field around the plasma and the anode. Diatomic oxygen molecules enter the housing and are polarized by the magnetic field and the resulting oxygen ions accelerated toward the plasma. The plasma excites and confines the oxygen ions long enough for them to strike the materials forming the cathode and anode, releasing positive ions of the cathode and anode materials which bind together and form the negatively-charged molecules $[MO_x]^-$.

Another important feature of the present invention is the negatively-charged molecule produced by the ion generator. The molecule has a higher molecular weight than substantially all the gasses contained in atmospheric air, therefore the air charge is denser, so the engine produces more torque and horsepower for the same amount of fuel, resulting in a more efficient engine with greater fuel economy.

Still another feature of the present invention is the adjustability of the ion generator and the concentration of negatively-charged molecules in the combustion gas supplied to the engine. The gap between the anode and cathode of the generator can be increased or decreased, and a resistor, preferably an adjustable resistor, is carded by the cathode so that the intensity of the plasma field can be changed or adjusted to control the output. In addition, a valve at the outlet of the generator can be adjusted to control the concentration of negatively-charged molecules in the combustion gas supplied to the engine.

Other features and advantages of the present invention will be apparent to those skilled in the art from a careful reading of the Detailed Description of a Preferred Embodiment presented below and accompanied by the drawings.

DETAILED DESCRIPTION OF A PREFERRED EMBODIMENT

Figure 1:
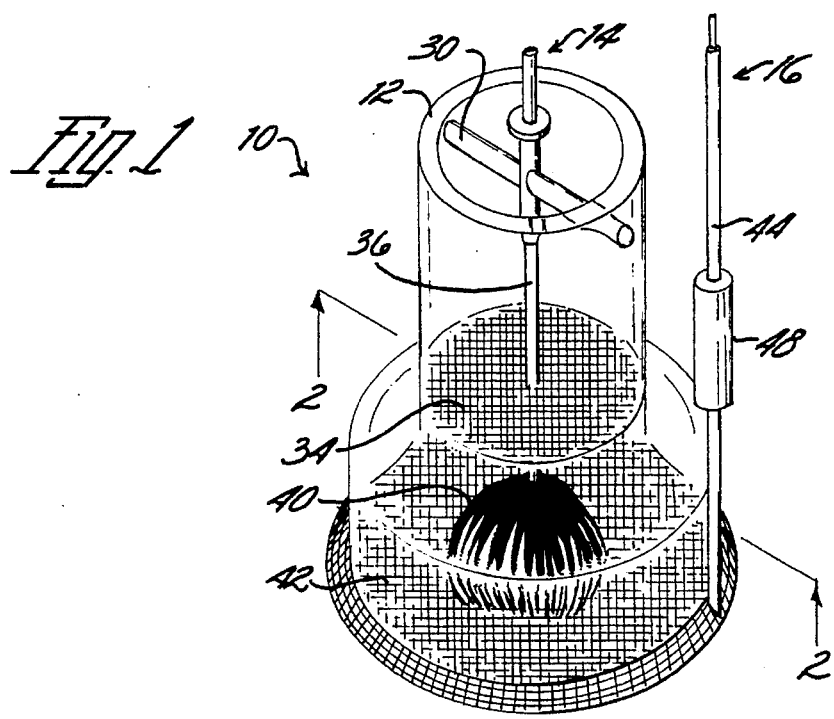
FIG. 1 is a perspective view of an ion generator according to a preferred embodiment of the present invention.

In the following description, similar components are referred to by the same reference numeral in order to simplify the understanding of the sequential aspect of the drawings.

The present invention is an apparatus and method for supplying ion-enriched combustion gas to an internal combustion engine. The apparatus produces negatively-charged molecules of the form $[MO_x]^-$, where M is a positive ion, O is oxygen, and x is a number having a value at least equal to three. In particular, x will equal three, four, five or more. The charged molecules are mixed with a combustion gas, preferably air, and transferred to the engine. The molecules are attracted towards the positive ionic charges at the cylinder and other places, reducing the repulsion of the positive ions that the induction system normally generates, allowing a more dense air charge to exist in the engine, thereby increasing the mass of the air charge. This increases the force, so that the air charge generates a longer bum and more power. More fuel is burned, creating more heat, creating more pressure, torque and horsepower.

Figure 2:
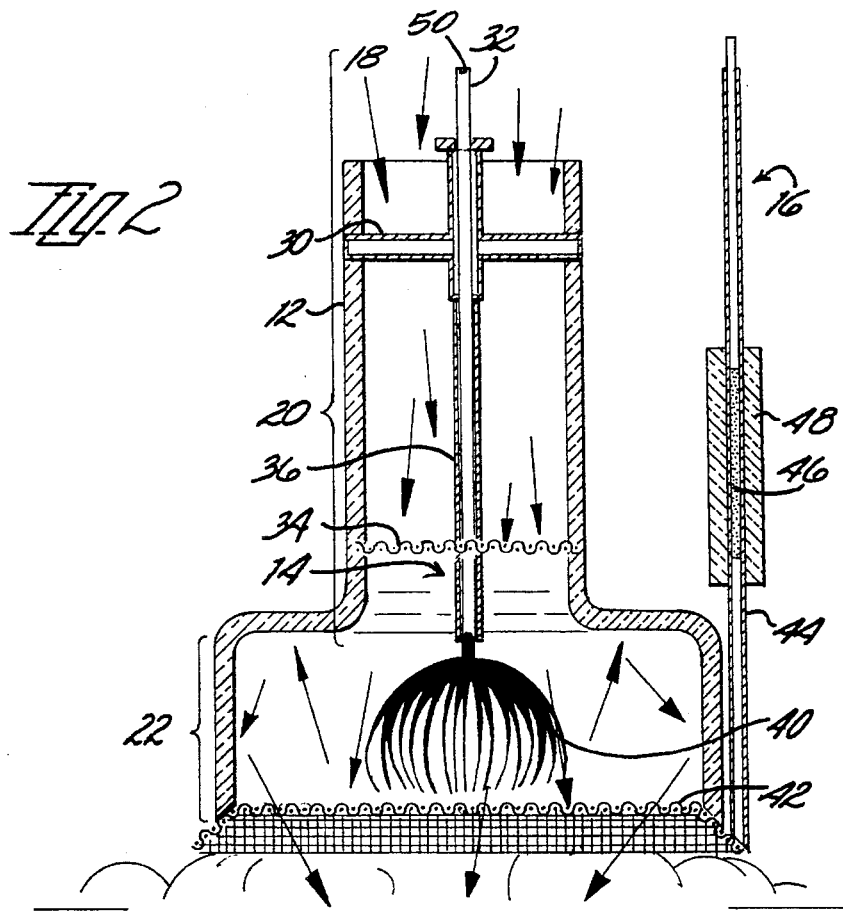
FIG. 2 is a side cross section of the ion generator of FIG. 1, taken along line 2—2.

Referring now to FIGS. 1 and 2, there is illustrated an apparatus for generating charged molecules (ions) according to a preferred embodiment of the present invention. The apparatus, generally indicated by the reference character 10, comprises a housing 12 made of a non-conducting, preferably insulating material, such as glass. Inside is an anode 14. On the end is a cathode 16. Anode 14 has two major portions: a first portion 20 for generating a long electric field; and a second portion 22 for generating a plasma field. The electric field and plasma field generate a magnetic field that pulls diatomic oxygen molecules apart, and accelerates them forward toward the plasma and ultimately out of apparatus 10.

First portion 20 of anode 14 comprises a stator bar 30, an anode adjustment shaft 32, a grid 34, and an anode generator shaft 36, all at the same electrical potential. Stator bar 30 provides support for anode 14. Shaft 36 is relatively long so as to produce an elongated electric field in order to create and maintain a high level of ionization of the molecules passing through housing 12. Shaft 36 also acts as a stator to the anode adjustment shaft 32. When a substantially constant voltage is applied across anode 14 and cathode 16, the electrical field thus established along anode generator shaft 36 from stator bar to grid 34 generates a magnetic field oriented so that diatomic oxygen molecules entering housing 12 at 18 will be ionized and accelerated parallel to shaft 36. A voltage of approximately 20 KV is sufficient to generate the magnetic and plasma fields. Housing 12 maintains the oxygen ions, and other ions, at a high state of excitation as they continue through apparatus 10.

Second portion 22 of anode 14 cooperates with cathode 16 in establishing the plasma field. Second portion 22 comprises a plurality of electrodes 40 that flare outwardly from a common attachment to anode adjustment shaft 32. Electrodes 40 are wider at one end, the end where they are in electrical and physical attachment with each other and adjustment shaft 32, and taper toward the opposing end, where they are narrower and separated. Alternatively, electrodes 40 can be interwoven, or in some other configuration, so long as they are separated from each other at the end nearer to cathode 16. The magnetic field encloses the plasma field and assists in the escape of the charged molecules from the confining plasma field.

Cathode 16 is in the form of a grid 42 and a cathode conductor 44 with a cathode resistor 46 and resistor housing 48. Grid 42 can also be in the form of a mesh or perforated plate, so long as it has a plurality of throughholes through which charged molecules, indicated by arrows in FIG. 2, can pass.

Anode adjustment shaft 32 threadedly engages anode generator shaft 36 and has a slot 50 at the end so that, by turning shaft 32, shaft 32 can be advanced or withdrawn to adjust the size of the gap between anode 14 and cathode 16. An adjustable anode shaft 32 having approximately 32 turns per inch allows sufficient fineness of control for selecting a suitable gap spacing.

Cathode 16 has resistor 46 located within resistor housing 48 of cathode conductor 44 to load cathode 16 and thereby set the intensity of the plasma. If the voltage is 20 KV, the current through apparatus 10 is preferably approximately 250 μamps, which produces negligible heat. A fan may optionally be used to drive air from the anode side to increase throughput, but is not required since the magnetic field supplies sufficient pressure through the acceleration of the oxygen ions. Thus, no cooling or other special treatment of the incoming air is required in order to produce the charged molecules.

Anode 14 is a "sacrificial anode," that is, the material of anode 14 is consumed during operation of apparatus 10 so that the anode must eventually be replaced. Anode 14 and cathode 16 are preferably two different conductors and also preferably soft, electron-rich materials so that their positive ions can be released by the incident oxygen ions. Soft metals, carbon, fiberglass, or other conductors and semiconductors are examples of electrode materials that will be satisfactory. In particular, the anode could be made of bronze and the cathode of aluminum, alternatively, the anode could be aluminum or an aluminum alloy and the cathode of some other material. Most preferably, anode 14 is made of aluminum or an aluminum alloy. However, there needs to be a source of positive ions and there needs to be an anode and a cathode, preferably an anode and cathode made of different materials. The present apparatus combines these requirements in an anode and cathode made of conductor materials that will release positive ions when struck by oxygen ions accelerated by the magnetic field.

Figure 3:
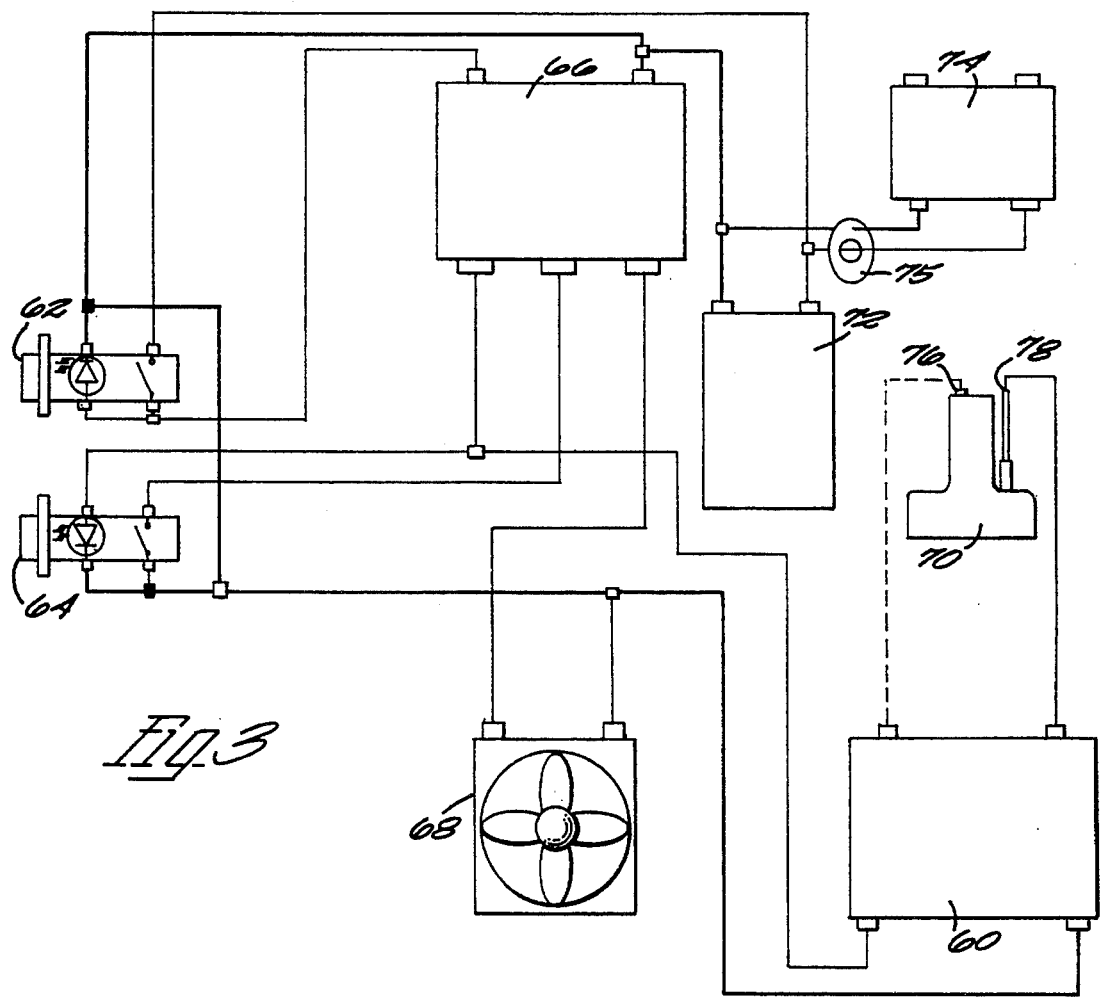
FIG. 3 is a schematic showing the ion generator of FIG. 1 in a complete system.

In use, as illustrated in FIG. 3, a generator electronic module 60 is activated by two switches 62, 64. Switch 64 is a main power switch which activates a control electronics module 66 and a fan 68. Switch 64 is preferably a "momentary" switch, that is, it does not remain in the "on" position. Switch 64 signals control electronics module 66 to activate generator electronics module 60 which in turn activates apparatus 70. Apparatus 70 is preferably operated continuously. However, apparatus 70 may be turned off by generator electronics module 60 after a preselected period of time if desired. Fan 68 may remain on for a while longer to purge the system.

Power is supplied either by a battery 72 or a standard source of 120 VAC 74 rectified by a rectifier 75. Battery 72 may be a standard automobile-type battery that supplies a fixed DC voltage, preferably 12 V or higher.

Generator electronics module 60 generates a high voltage, preferably about 20 KV, which is applied across anode 76 and cathode 78 of apparatus 70. When a voltage is applied across anode 76 and cathode 78, a high-density electrical field is generated which in turn generates a high density plasma field around and between anode 76 and cathode 78, which in its turn generates a high density magnetic field inside apparatus 70. The magnetic field encloses and encapsulates the plasma field and runs the length of the electrical field. The magnetic field polarizes the incoming diatomic oxygen molecules, which are then separated into oxygen ions by magnetic repulsion, electrical excitation and high velocity molecular collisions. The magnetic field accelerates the oxygen ions toward anode 76 and cathode 78. The oxygen ions strike anode 76 and cathode 78, causing positive ions from the anode and cathode conductor material to be released. In the plasma, these ions reach a high level of excitation and a large number of excitation collision coincidences. The oxygen ions bond with each other and with ions released from anode 76 and cathode 78 to form negatively-charged, triatomic, quadratomic, and quintatomic molecules of the form $[MO_x]^-$ where M is a positive ion, O is oxygen and x is a number at least equal to 3. These molecules, having more momentum than the individual oxygen ions, escape the plasma and charge toward cathode 78. The charged molecule will pass through holes in cathode 78 and exit apparatus 70.

The materials used for anode 76 and cathode 78 determine the activity level of the negatively-charged molecules $[MO_x]^-$, the distance traveled by the molecules, and the lifetime of the molecules. Ozone ($O_3$), for example, is neutral with an average lifetime of approximately 8 hours. The charged molecules formed by apparatus 70 typically have an average lifetime that depends on the time that elapses before the molecules reach a surface. The molecules neutralize within a few seconds of striking a surface. Because of their high velocity, and ionic attraction between the negatively-charged molecules and the positive charge on automobile engine components, the molecules act as though they were lighter than air.

Figure 4:
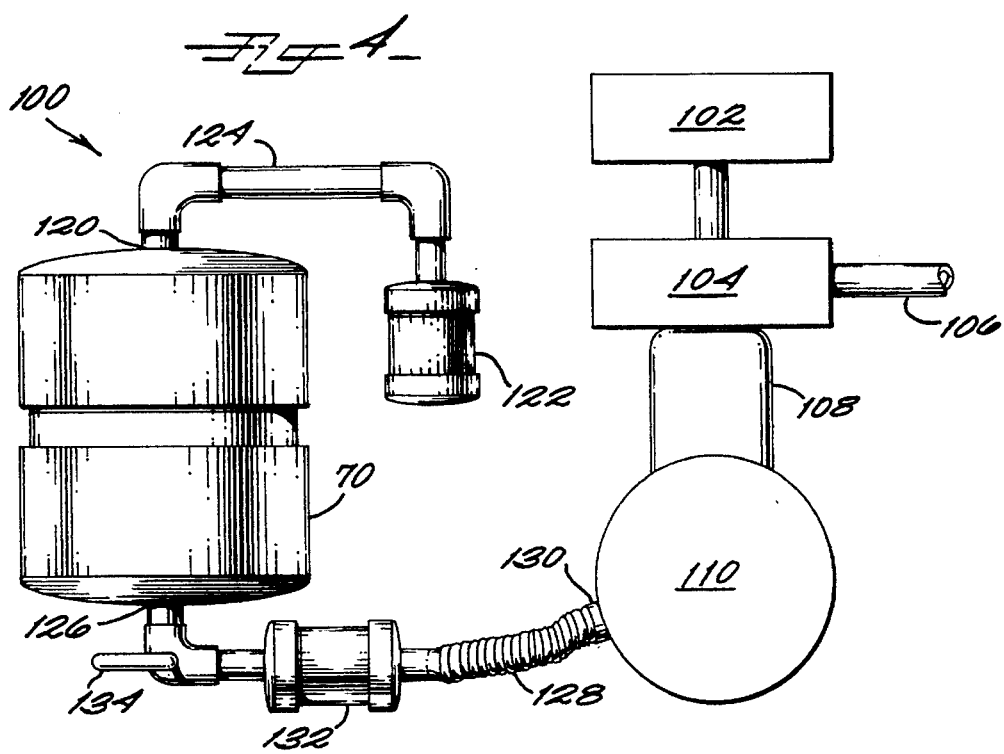
FIG. 4 is a schematic showing an apparatus for supplying combustion gas according to a preferred embodiment of the invention.

Referring now to FIG. 4, there is shown an apparatus 100 according to a preferred embodiment of the present invention. Apparatus 100 includes an internal combustion engine 102 such as is known in the art, with a carburetor 104, a fuel inlet 106, an air inlet 108, and an air intake filter assembly 110. An ion generating apparatus such as apparatus 70 has an air inlet 120, which may be connected to an air filter 122 by a conduit 124. Apparatus 100 may operate on any suitable combustion oxygenated gas, including but not limited to air, oxygen-enriched air, and $N_2O$-enriched air.

A conduit 128, preferably a length of flexible tubing, connects an outlet 126 of apparatus 70 to an inlet 130 of filter assembly 110. Apparatus 100 may include a flame arrestor and blowback valve, represented as a device 132 disposed in conduit 128. Device 132 may include any suitable type of flame arrestor, for example, an assembly of screens, perforated plates, or metal-gauze packing. Device 132 also preferably includes a blowback valve to prevent gases and/or fuel from backing up and entering apparatus 70. A valve 134 controls the amount of negatively-charged molecules that exit apparatus 70, thereby controlling the concentration of negatively-charged molecules in air (or other combustion gas) supplied to carburetor 104.

Figure 5:
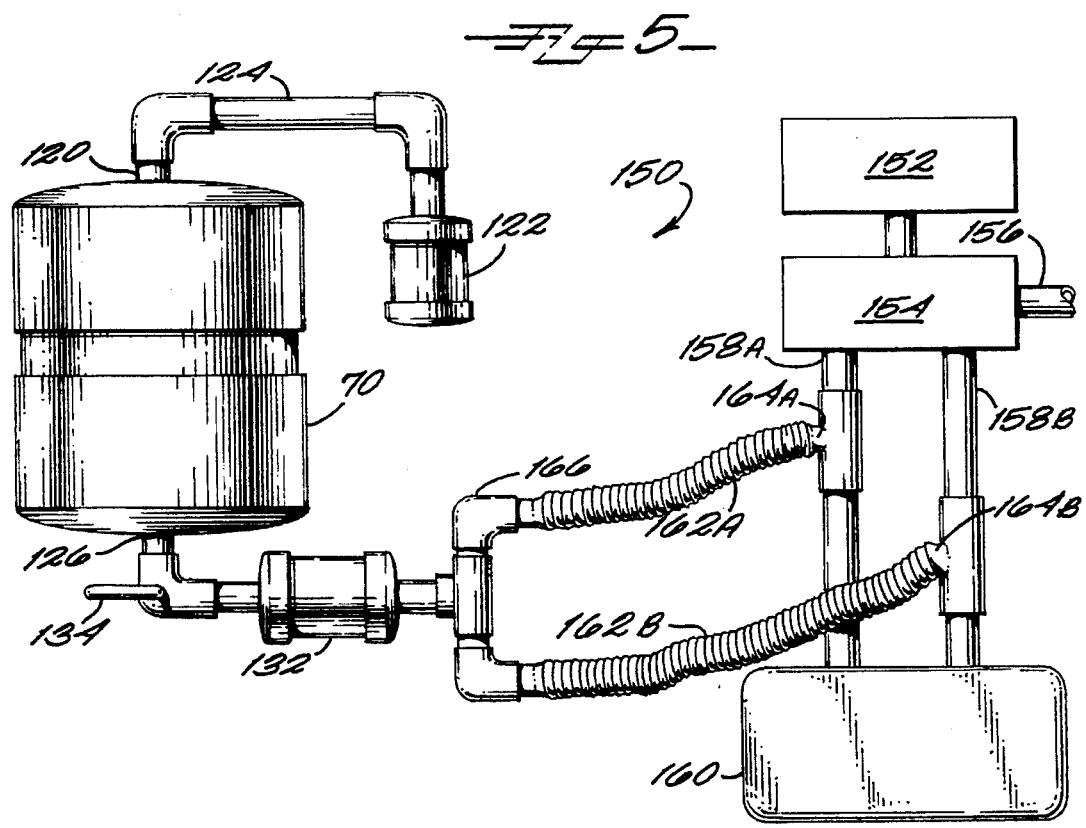
FIG. 5 is a schematic showing an apparatus for supplying combustion gas according to another preferred embodiment of the invention.

An apparatus 150 according to another preferred embodiment of the present invention is shown in FIG. 5. Apparatus 150 includes an internal combustion engine 152 with a fuel injection system 154, a fuel input 156, dual air inputs 158a, 158b, and an air intake filter assembly 160. Conduits 162a, 162b connect outlet 126 of apparatus 70 to couplers 164a, 164b in conduits 158a, 158b, respectively. Conduits 162a, 162b are connected to device 132 (if present) via a coupler 166. Thus, negatively-charged molecules produced by apparatus 70 are introduced into the air stream after filter assembly 160, but prior to the fuel injection system 154 and the throttle body of engine 152. Alternatively, conduits 162a, 162b may be connected directly to filter assembly 160. Like apparatus 100, apparatus 150 may operate on any suitable combustion gas, including but not limited to air, oxygen-enriched air, and $N_2O$ enriched air.

In both apparatus 100 and apparatus 150, negatively-charged molecules are introduced into the air-fuel mixture supplied to an internal combustion engine (engine 102, 152). Air enters apparatus 70 via filter 122, which filters out particulates and ensures that substantially dust-free air enters apparatus 70. Negatively-charged molecules are produced in apparatus 70 as described above, and exit apparatus 70 at outlet 126. Valve 134 is used to adjust the concentration of charged molecules in the air supplied to carburetor 104 or fuel injection system 154, preferably to a value between 0 and approximately 120 parts per million (ppm). However, higher concentrations may also be useful, depending on the type of engine and gasoline, and ambient environmental conditions. The mixture of air and charged molecules passes through device 132, which prevents engine backfires from damaging apparatus 70, and enters conduit 128 (or conduits 162a, 162b).

At this point, the negatively-charged molecules are heavily ionized and carry attached $O_3$, $O_4$, $O_5$, and so forth. The charged molecules are attracted towards the positive ionic charges at the surfaces of engines 102, 152, reducing the effect of repulsion between positive ions and thereby allowing a denser, heavier air charge to exist in the engine. The increase in the mass of the air charge, together with the standard induction system velocity of the engine, increases the force of the air charge and pushes more air into the cylinders of engine 102, 152. Since a greater mass of air is present, the burn is longer and more power is produced for the same amount of gasoline.

In addition, the negatively-charged molecules produced by apparatus 70 carry heavy, unstable polyatomic oxygen molecules $O_x$, where $x \geq 3$. Thus, the oxygen charge (the amount of oxygen supplied to engine 102, 152) is enriched by a factor that depends on the concentration of negatively-charged molecules $[MO_x]^-$ in the air entering carburetor 104 or injection system 154. The oxygen charge may be higher by a third or more over that supplied by ambient air alone, which contains largely diatomic oxygen molecules ($O_2$) rather than the polyatomic molecules generated by apparatus 70. Since more oxygen is supplied to engine 102, 152, the burn is longer and more fuel is burned, creating more heat, more expansion of hot gases, and increased pressure, resulting in more torque and horsepower for the same percentage of throttle.

Apparatus 70 produces nitrous oxide ($N_2O$) in addition to the above-described negatively-charged molecules. Nitrous oxide has a higher molecular weight and density than air, which contains mostly nitrogen ($N_2$), therefore, it is used in the field of automobile racing to increase the horsepower output of internal combustion engines. Nitrous oxide is an unacceptable additive for day-to-day driving because it is supplied in cylinders containing only a few cubic yards of compressed gas. However, apparatus 70 produced a steady, controllable supply that, in conjunction with negatively-charged molecules $[MO_x]^-$, substantially increases the power output of engine 102, 152.

When the air charge (that is, air enriched with negatively-charged molecules $[MO_x]^-$ and $N_2O$) enters the cylinder of engine 102, 152, it has a substantially greater oxygen density than the density of atmospheric air. Molecules $[MO_x]^-$ do not break down until the cylinder temperature reaches approximately 602° F., when they break apart and convert into diatomic oxygen ($O_2$). This delay in the breakdown of molecules $[MO_x]^-$ allows for a smoother, hotter burn than occurs with a naturally-aspirated engine (i.e. where the air charge is supplied by atmospheric air alone), retards detonation and promotes a longer burn because the burn is progressive. Therefore, more power is produced from less fuel, that is, less throttle percentage is needed to produce the same engine output, whether measured in speed or work.

It will be apparent to those skilled in the art that many changes and substitutions can be made to the preferred embodiment herein described without departing from the spirit and scope of the present invention as defined by the appended claims.

What is claimed is:

1. Apparatus for supplying a mixture of combustion gas and fuel to an internal combustion engine, said apparatus for use with a source of combustion gas and a source of fuel, said apparatus comprising:

a housing having a first inlet for combustion gas from said source of combustion gas to enter said housing, a second inlet for fuel from said source of fuel to enter said housing, and an outlet in fluid connection with said engine;

means for mixing said combustion gas and said fuel, said mixing means positioned in said housing; and means for generating negatively-charged molecules having the formula $[MO_x]^-$, where M is a positive ion of said electrically conducting material, O is oxygen, and x is a number $\geq 3$, said generating means in fluid connection with said first inlet so that said negatively-charged molecules are mixed with combustion gas supplied to said mixing means.

2. The apparatus as recited in claim 1, wherein said generating means further comprises:

means for forming a plasma field;

an electrically conducting material positioned in said plasma field;

means for separating oxygen into oxygen ions;

means for accelerating said oxygen ions toward said plasma field;

means for confining said oxygen ions in said plasma field so that said oxygen ions strike said material and release positive ions therefrom, whereby at least a portion of said oxygen ions become bound to said positive ions to form said negatively-charged molecules.

3. The apparatus as recited in claim 1, wherein combustion gas entering said mixing means has a concentration of said negatively-charged molecules, further comprising means for controlling said concentration.

4. The apparatus as recited in claim 1, wherein said generating means has an inlet connected to a source of oxygen and an outlet connected to said first inlet of said mixing means, further comprising means for preventing particles from entering said inlet of said generating means when oxygen enters therein.

5. The apparatus as recited in claim 1, further comprising:

a conduit connecting said generating means to said first inlet; and a flame arrestor disposed in said conduit.

6. The apparatus as recited in claim 1, further comprising;

a conduit connecting said generating means to said first inlet; and a blowback valve disposed in said conduit, said blowback valve allowing passage of said negatively-charged molecules from said generating means to said mixing means, said blowback valve preventing passage of fluid from said mixing means to said generating means.

7. The apparatus as recited in claim 1, wherein said mixing means further comprises a carburetor with an air intake filter, said filter having an inlet adapted for receiving air and an outlet in fluid connection with said carburetor, and wherein said apparatus further comprises a conduit connecting said generating means to said inlet of said air intake filter.

8. The apparatus as recited in claim 1, wherein said mixing means further comprises a fuel injector with an air intake plenum, and wherein said apparatus further comprises at least one conduit connecting said generating means to said air intake plenum.

9. Apparatus for supplying a mixture of combustion gas and fuel to an internal combustion engine, said apparatus for use with a source of combustion gas and a source of fuel, said apparatus comprising:

means for mixing combustion gas and fuel, said mixing means having a first inlet for combustion gas from said source of combustion gas to enter said mixing means, a second inlet for fuel from said source of fuel to enter said mixing means, and an outlet in fluid connection with said engine;

a housing made of a non-electrically conducting material, said housing having a first opening for oxygen from a source of oxygen to enter said housing and a second, opposing opening;

a cathode positioned in said housing near said first opening, said cathode having a plurality of throughholes through which said oxygen can pass; and an anode positioned in said housing and spaced apart from said cathode so as to define a gap therebetween, said anode having a first portion near said second opening and an adjacent second portion, said first portion formed to accelerate ions electromagnetically from inside said housing through said second opening when said source of direct electrical current is applied across said anode and cathode, said second portion being in the form of a plurality of electrodes flaring outwardly and toward said cathode so as to form a plasma between said second portion and said cathode when said electrical current is applied to said cathode and said anode, said plasma ionizing said oxygen entering said housing through said first opening and producing charged molecules that are accelerated by said first portion of said anode through and from said housing, said second opening in fluid connection with said first inlet of said mixing means so that said charged molecules are mixed with combustion gas and fuel supplied to said engine.

10. The apparatus as recited in claim 9, wherein said anode and said cathode are made of different conductors.

11. The apparatus as recited in claim 9, wherein said anode is made of a material selected from the group consisting of aluminum and aluminum alloys.

12. The apparatus as recited in claim 9, wherein combustion gas entering said mixing means has a concentration of said negatively-charged molecules, further comprising means for controlling said concentration.

13. The apparatus as recited in claim 9, further comprising:

a conduit connecting said second opening to said first inlet; and a flame arrestor disposed in said conduit.

14. The apparatus as recited in claim 9, further comprising;

a conduit connecting said second opening to said first inlet; and a blowback valve disposed in said conduit, said blowback valve allowing passage of said negatively-charged molecules from said generating means to said mixing means, said blowback valve preventing passage of fluid from said mixing means to said generating means.

15. The apparatus as recited in claim 9, wherein said first portion of said anode further comprises a conducting rod having a first end and a second end, said first end positioned near said first opening, said second end electrically connected to said second portion, so that, when a source of direct electrical current is applied to said anode and said cathode, said second portion forms a plasma with said cathode that ionizes oxygen entering said first opening, said conducting rod accelerating electromagnetically ions escaping said plasma toward said second end and from said housing; and means for mixing said ions with air.

16. Apparatus for powering a vehicle, comprising:

an internal combustion engine;

means for supplying fuel to said engine;

means for supplying combustion gas to said engine; and means for generating negatively-charged molecules having the formula $[MO_x]^-$, where M is a positive ion of said electrically conducting material, O is oxygen, and x is a number $\geq 3$, said generating means in fluid connection with said gas-supplying means so that said negatively-charged molecules are mixed with combustion gas supplied to said engine.

17. The apparatus as recited in claim 16, wherein said generating means further comprises:

means for forming a plasma field;

an electrically conducting material positioned in said plasma field;

means for separating said oxygen into oxygen ions;

means for accelerating said oxygen ions toward said plasma field;

means for confining said oxygen ions in said plasma field so that said oxygen ions strike said material and release positive ions therefrom, whereby at least a portion of said oxygen ions become bound to said positive ions to form said negatively-charged molecules.

18. The apparatus as recited in claim 16, wherein said generating means further comprises:

a housing made of a non-electrically conducting material, said housing having a first opening for oxygen to enter said housing and a second, opposing opening, said second opening in fluid connection with said gas-supplying means;

a cathode positioned in said housing near said first opening, said cathode having a plurality of throughholes through which said oxygen can pass;

an anode positioned in said housing and spaced apart from said cathode so as to define a gap therebetween, said anode having a first portion near said second opening and an adjacent second portion, said first portion formed to accelerate ions electromagnetically from inside said housing through said second opening when a source of direct electrical current is applied across said anode and cathode, said second portion being in the form of a plurality of electrodes flaring outwardly and toward said cathode so as to form a plasma between said second portion and said cathode when said electrical current is applied to said cathode and said anode, said plasma ionizing said oxygen entering said housing through said first opening and producing charged molecules that are accelerated by said first portion of said anode through and from said housing, at least a portion of said charged molecules passing through said second opening and entering said gas-supplying means.

19. The apparatus as recited in claim 1, wherein combustion gas entering said engine contains a concentration of said negatively-charged molecules, further comprising means for controlling said concentration.

20. The apparatus as recited in claim 16, further comprising;

a conduit connecting said outlet to said gas-supplying means;

a flame arrestor disposed in said conduit; and a blowback valve disposed in said conduit.

* * * * *